United States Patent [19]

Stewart

[11] 3,992,627

[45] Nov. 16, 1976

[54] DIAGNOSTIC APPARATUS

[75] Inventor: Peter Anthony Eabry Stewart, Bristol, England

[73] Assignee: Rolls-Royce (1971) Limited, London, England

[22] Filed: Apr. 9, 1975

[21] Appl. No.: 566,279

Related U.S. Application Data

[63] Continuation of Ser. No. 428,713, Dec. 27, 1973, abandoned.

[30] Foreign Application Priority Data

Jan. 6, 1973 United Kingdom............... 00873/73

[52] U.S. Cl............................... 250/312; 250/360; 250/460
[51] Int. Cl.².................................... G01M 23/00
[58] Field of Search..................... 250/460, 360, 312

[56] References Cited
UNITED STATES PATENTS 2,745,969   5/1956   Keller ................................. 250/360
2,998,518   8/1961   Guntert.............................. 250/460
3,809,900   5/1974   Steffel................................ 250/460

OTHER PUBLICATIONS

Firestone Inspects Tires with X-Ray System, "Canadian Controls and Instruments," July 1970, vol. 9, No. 7, pp. 36,37.
"Radiography—Turbines," by Pullen Published Mar. 1971.
Radiography of Gas Turbines in Motion by Stewart, 65CME, May 1972.

Primary Examiner—Harold A. Dixon
Attorney, Agent, or Firm—Stevens, Davis, Miller & Mosher

[57] ABSTRACT

This invention concerns an apparatus for producing real time and recorded pictures of the internal parts of a gas turbine engine, during the operation of the engine, the pictures being produced by directing high energy X-rays at the engine and deriving the results via a fluorescent screen and an image intensifier.

10 Claims, 10 Drawing Figures

| Gap | Gap size minimum | Engine condition | Gap size maximum | Engine condition |
|---|---|---|---|---|
| Stator tip to spacer | .034 ins | 101% max. r.p.m. | .074 ins | 36% max. r.p.m. |
| Upstream rotor to spacer | .034 ins | 101% max. r.p.m. | .041 ins. | 36% max. r.p.m. |
| Downstream rotor to spacer | .015 ins | Static | .039 ins | 95% max. r.p.m. |

DIAGNOSTIC APPARATUS

This is a continuation of application Ser. No. 428,713 filed Dec. 27, 1973, now abandoned.

This invention relates to improvements in diagnostic apparatus and especially to diagnostic apparatus suitable for reducing the time involved in the development of prime movers.

For example the performance of a gas turbine engine is affected greatly by the efficiency of the seals associated with its major components. The position and operating clearances of such seals are interdependent on the thermal gradients and gas pressures within the engine and these parameters are in turn dependent on the operating conditions of the engine. There has long been a need for a method of quickly investigating the positions of these seals during operation of the engine. Past techniques have involved the use of abradable pegs and markers which necessitated dismantling the engine after each run and which created difficulties in determining the effects of transient conditions.

It has previously been proposed to subject a gas turbine engine to electromagnetic radiation of the X-ray wavelengths and to record the images so produced as radiographs on photographic plates. These radiographs have then been examined and interpreted to yield an understanding of the positions of the various components within the engine. The problems associated with seals in a gas turbine engine are most acute in the vicinity of the turbine.

The beam for an X-ray radiograph of a turbine has to penetrate several thicknesses of relatively dense metal. X-ray theory predicts that maximum penetration occurs with such metals at a wavelength for the radiation corresponding to 8 MeV and this radiation has therefore been used. From investigations into the taking of X-ray radiographs it is known that it is desirable to reduce the time needed to take each radiograph. Reduction of the time for each exposure is desirable to freeze transient conditions and improve the resolution of the radiograph. It is also known that better resolution is obtained by the use of fine grained film but that this requires either a relatively longer exposure time or a relatively higher power than for a coarse grained film, thus emphasising the importance of a high power source to achieve good resolution of transient conditions.

In order to examine the engine throughout its operating cycle, a series of radiographs has had to be taken and these have formed the basis for plotting the movements of engine components.

Radiographs taken of an engine operating under steady state conditions have in the past used exposure times of the order of two to three seconds whilst those for transient conditions have been recorded on an exposure lasting about 0.1 sec.

Transient conditions such as accelerations, decelerations, surges and thrust reversals have all been previously recorded by the radiograph technique and the following procedural sequence for an acceleration of the engine from idling speed to full speed may be considered as typical of what it has hitherto been necessary to do.

A photographic plate is arranged to receive the transmitted beam through the engine which is running at idling speed. All personnel are evacuated from the site enclosing the engine and its environs, the site is locked and a rigorous safety procedure followed, the X-ray source is energized and a radiograph taken at 0 secs with an exposure of 0.1 secs. The X-ray set is de-energized and the all clear signal given, the site is unlocked, the photographic plate is charged, personnel are evacuated as before and a second shadowgraph is taken at + 5.0 secs whilst the engine is accelerated from its idling condition. The engine is then decelerated to idling, the photographic plate changed, and a second exposure at + 10.0 secs is taken as the engine is again accelerated from idling. The procedure is repeated taking radiographs at times corresponding to successive 5 second intervals from 0 secs to 50.0 secs, 50 seconds being a typical time interval over which investigations have been carried out whilst an engine is accelerated or decelerated between idling to maximum speed.

Thus to achieve a complete picture of what is happening within a gas turbine engine a series of radiographs has had to be taken and each radiograph has required a lengthy procedure to be followed. Even after following this procedure, the possibility remained that undetected events had taken place within the gas turbine engine both during the gaps in the photographic sequence and subsequent to the last radiograph being taken. Indeed the on-off sequence, with the resultant lag of certain engine components in thermal response, may produce an unrealistic picture of what is happening within the engine.

The present invention is directed towards an improved method of investigating the cyclic changes within a gas turbine engine and to the elimination of some of the disadvantages of the present techniques.

According to the present invention there is provided diagnostic apparatus comprising a source capable of supplying electromagnetic radiation in the energy range 5 to 12 MeV and of power greater than 250 Rads per minute, means for directing the source towards a prime mover, during the operation of the prime mover, the prime mover having parts capable of relative movement, a fluorescent screen arranged to receive the radiation transmitted through the prime mover, means for scanning said screen and amplifying the fluorescent image thereon and means for recording said amplified image for examination of relative movement of the parts.

Also according to the present invention a method of investigating a prime mover, during operation thereof, the prime mover having parts capable of relative movement, comprises the steps of directing electromagnetic radiation in the energy range 5 to 12 MeV and of power greater than 250 Rads/minute towards the prime mover, receiving the radiation transmitted through the prime mover on a fluorescent screen to produce a fluorescent image, amplifying the fluorescent image formed on the fluorescent screen and recording said amplified image for examination of said relative movement of the parts.

Preferably said scanning and fluorescent image amplifying means is shielded against the radiation.

Also according to this invention a method of investigating a prime mover comprises the steps of, recording said amplified image on a photographic film, measuring the intensity distribution on the film and comparing this intensity distribution with either, known static dimensional relationships of the parts of the prime mover corresponding to the image, or with intensity distributions of similar images measured at different operating conditions of the prime mover, and deducing a numerical value for the dimensional relationship of the parts of the prime mover corresponding to the conditions at which said amplified image was obtained.

An embodiment of the invention will now be described by way of example only with reference to the accompanying drawings wherein.

Figure 1:
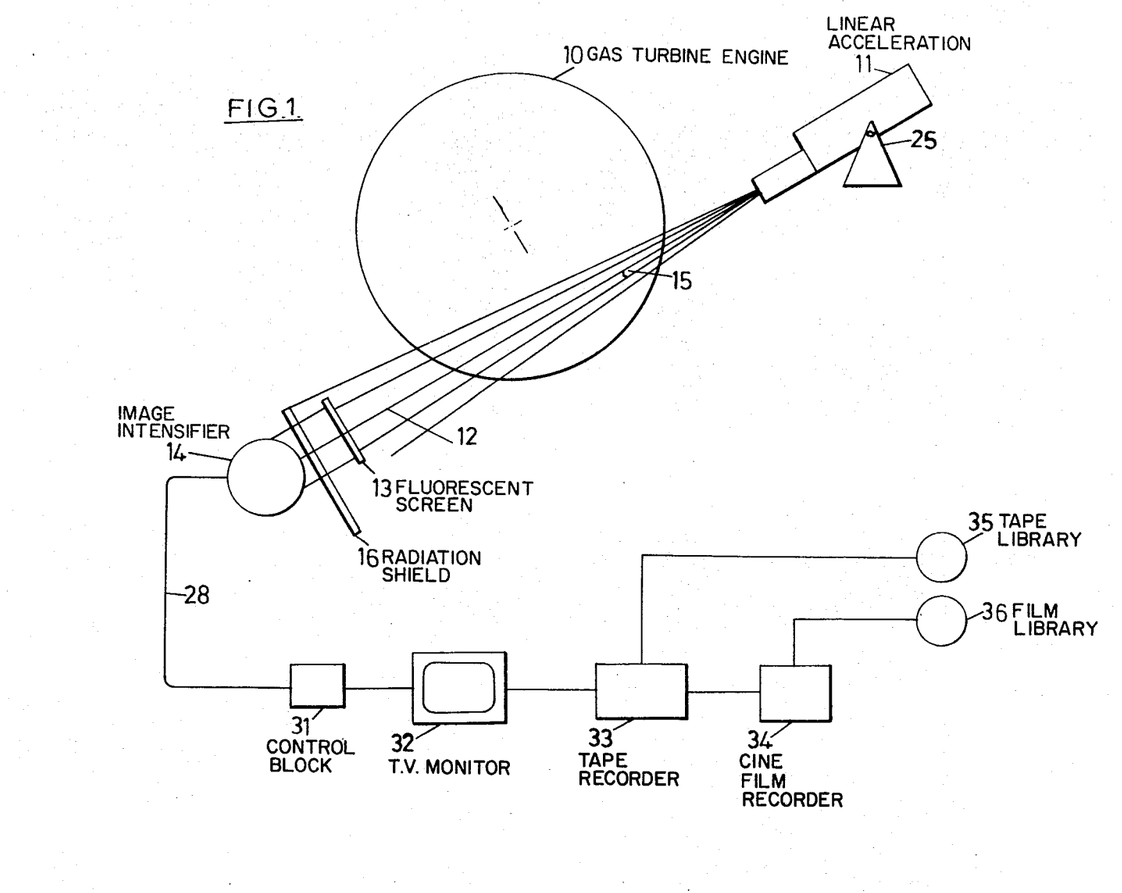
FIG. 1 is a schematic view of an apparatus according to the invention.

In FIG. 1 a gas turbine engine 10 is shown supported in a test bed (not shown) and is connected, according to conventional practice, to fuel an electrical supplies and such instrumentation as may be necessary for controlling the engine.

A linear accelerator 11 generates electrons and accelerates them to an energy of 8 MeV. The electrons then strike a target and generate X-rays ranging in energy up to 8 MeV. The distribution of energies is a characteristic of the target material and generally shows two discrete maxima. In this invention a target was chosen having a strong X-ray emission corresponding to 8 MeV. In general at the high frequencies associated with electromagnetic radiation in the X-ray region it is convenient to work in terms of energy measured in mega electro-volts rather than frequency, the transformation between energy and frequency for one quantum of radiation being that discovered by Planck.

The X-rays emerge from the linear accelerator through a collimator which limits the angle of divergence of the beams. The X-rays leave the target from a focal spot of the order of two millimeters in diameter. Better resolution may be achieved with a smaller focal spot and a reduction of the spot size to one millimeter in diameter, for the apparatus herein described, has yielded the expected improvement in resolution and at the same time produce an unexpected improvement in maximum output power of the device from 1500 Rads/-min to 1600 Rads/min as measured one meter from the target along the normal ray. The reduction in focal spot size is effected by narrowing the electron beam before its impingement on the target and the power gain is thought to be due to having a more unidirectional stream of electrons impinging on the target.

The X-rays emerge from the linear accelerator in a divergent beam, the normal ray 12 being directed through that point of the prime mover of which examination is desired. The transmitted radiation is incident upon a fluorescent screen 13 associated with the image intensifier system 14 shown in more detail in FIG. 2. The screen 13 has a circular aperture and receives radiation from a cone of semi-solid angle 15.

A radiation shield 16, constructed from several sheets of lead to a total thickness of about three centimeters reduces the radiation incident on the image intensifier system 14, thereby substantially preventing the generation of spurious electrons within the light intensifier. These spurious electrons are very undesirable as they are further amplified by the amplification process within the image intensifier, thus forming a large noise signal at the output which considerably reduces the quality of the information signal.

The signal output from the image intensifying system passes by shielded cable 28 through a control block 31 to a television monitor 32. The control block allows the gain of the image intensifying system, the contrast, the magnification and the polarity of the picture to be adjusted to produce the best possible picture on the monitor 32. The polarity change mechanism enables darker areas on the television monitor 32 to be seen as light areas and vice-versa. The signal received by the television monitor is recorded on a video tape recorder 33 and a cine film recorder 34. The records from the two recorders are then stored in tape and film libraries 35, 36 respectively.

Figure 2:
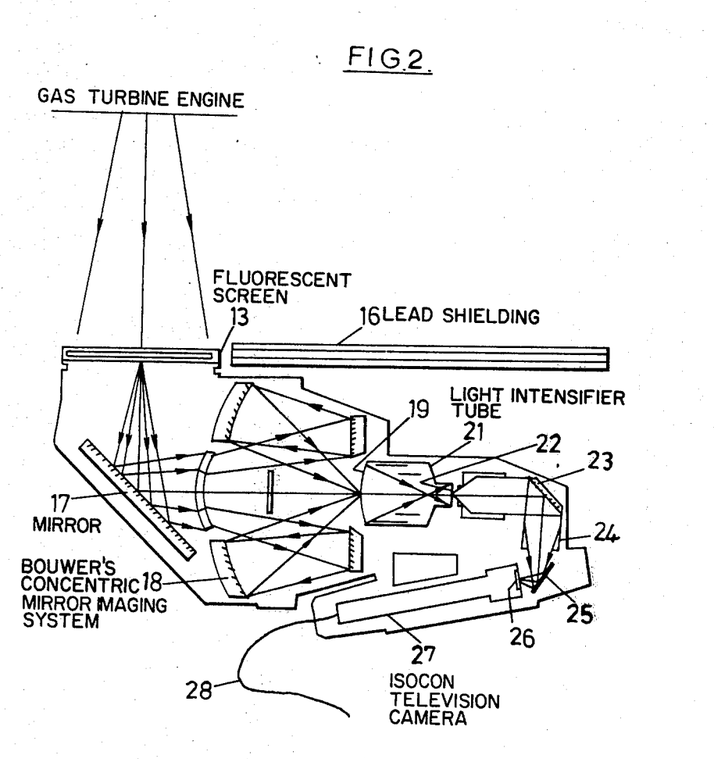
FIG. 2 is a diagrammatic view of the image intensifying system.

Referring now to FIG. 2, light from the fluorescent screen is reflected through 90° by a mirror 17 and the reflected light is gathered by a Bouwer's concentric mirror system 18 and the image reproduced on the front fluorescent screen 19 of a light intensifier tube 21. The image is intensified and the intensified image appearing on the rear screen 22 is deflected by a mirror 23, focused by a lens system 24 and relected by a further mirror 25 on to the screen 26 of an Isocon Television camera tube 27. It is desirable to use an image intensifying system similar to the one described where the intensifier does not lie directly behind the fluorescent screen in line with the incoming radiation, for in such a configuration it is very difficult to shield the intensifier from the radiation.

In a modification (not shown) it is proposed to replace the mirror 25 with a half silvered mirror and to directly record the image as seen on the back of the light intensifier on cine film, thus elimating any possible distortion through the Isocon camera tube. It will be appreciated that with a half silvered mirror the television monitor can be retained, but that a power increase from the linear accelerator may be necessary to make up for the signal losses at the half silvered mirror. In a further alternative the mirror may be removed altogether and only a cinematic record produced.

The selection of a suitable screen 13 for the image intensifier is very important to the extent that it has hitherto not been considered possible to achieve television pictures of X-ray information at energies in excess of 4.5 MeV and at power levels anywhere near the order of magnitude necessary for penetration of the metal thicknesses found along a chord of the gas turbine engine as traversed by the normal ray 12.

A power of 250 Rads/min, as measured at a distance of one meter from the target along the normal ray, can be considered as an absolute minimum power necessary to produce a picture and in practice a minimum power of 750 Rads/min has been found acceptable on relatively small gas turbine engines. Generally, however, power levels of 1500 Rads/min and above are preferred. The grain size of the screen requires to be as fine as possible to provide the best resolution, and in order to produce enough contrast on the fluorescent screen for amplification by the light intensifier a thick screen must be used to derive sufficient excitation by the received X-rays. However, as the screen thickness is increased the light photons generated by the X-radiation are scattered internally in the screen and this reduces the sharpness of the images produced on the screen. In practice the technique has been developed to the state that it is the internal scattering in the screen that is the limiting factor in the sharpness of the image rather than the geometrical unsharpness of the image. The geometrical unsharpness is due to the use of a finite focal spot size and the divergence of the beam and it has been reduced by the use of a small focal spot, and by making the target to engine distance as large as possible and the engine to screen distance as small as possible.

A filter, made for example from copper, may be placed in front of the screen and this will help cut out some of the multiply scattered X-rays which produce a background noise signal on the screen. A filter comprising a sheet of copper 0.5 centimeters thick has been found efficacious.

It is not desirable to use energies in excess of 12 MeV, for above this level some metals used in the construction of a gas turbine engine may be become radioactive and attenuation of the signal becomes more significant. The optimum frequency corresponds to 8 MeV radiation and dose rates have been used of up to 1600 Rads/min.

The screen and image intensifying stems are mounted on a platform of the engine test bed on a simple rack mechanism (not shown) which allows relative movement with the gas turbine engine and alignment of the normal ray.

The image intensifying system is preferably wrapped about with foam rubber to isolate it from seismic and acoustic vibrations. Isocon camera tubes are particulary sensitive to vibration which will reduce the quality of the picture.

The linear accelerator is mounted separately on its own framework 25 as seen in FIG. 1 to prevent vibration of the engine affecting the sensitive equipment inside the accelerator. It is found convenient to provide means for varying the position of the linear accelerator within its framework.

In lining up the linear accelerator, the engine, and the image intensifying system it has been found expedient to roughly align the apparatus and take one radiograph of the engine whilst it is not running. The relative positions of the linear accelerator and the image intensifying system may then be adjusted by an amount found by estimating the error from the picture on the television screen and applying the appropriate magnification factor for the relative distances of target to engine, engine to image intensifying system. With practice it has been found necessary to make only one trial run prior to establishing alignment of the apparatus.

A surprising result to emerge from this work has been that there is little or no vibration along the axis of an engine. It was generally thought that the vibration of an engine whilst running would be severe enough to reduce the sharpness of the image but this has not been found to be so.

It will be seen from FIG. 1 that the normal ray from the linear accelerator is directed through the engine at an angle of 45° to the vertical in a downward direction. The radiation transmitted from the engine and not absorbed by the screen or the shield is incident on the ground wherein a large part of it may be harmlessly absorbed.

Figure 3:
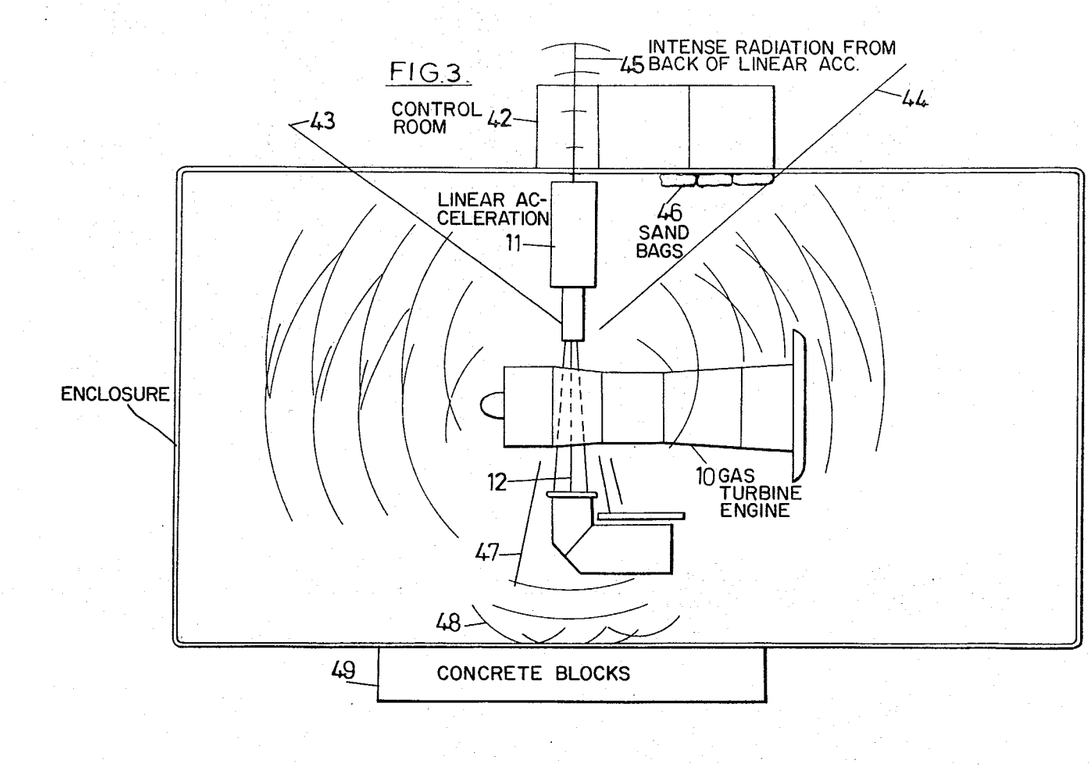
FIG. 3 illustrates the layout of the apparatus with reference to protection from radiation.

Reference to FIG. 3 will show an enclosure for the apparatus that has been developed to protect personnel from the potentially lethal effects of the radiation.

In FIG. 3 the immediate environs of the test cell and control house may be seen. The control room 42 is situated generally behind and to the right of the linear accelerator 11, in the area defined by the divergent lines 43, 44 and thus receives no direct, and very little reflected radiation. There is a fairly intense radiation beam 45 which emerges from the back of the linear accelerator in the opposite direction to the normal ray 12; however, because of the inclination of the accelerator this beam passes well over the top of the building and is harmlessly attenuated by the atmosphere after travelling only a relatively small distance, no hazard is therefore presented to overflying aircraft etc. The windows of the control room may be of lead glass, and sandbags 46 can be strategically positioned to protect personnel within the control room. Radiation 47 transmitted through the engine and not absorbed, and radiation 48 reflected from the ground is further attenuated by large extra dense concrete blocks 49 placed along the edge of the site forward of the image intensifying system.

Scattered radiation and radiation reflected from the internals of the engine are much less intense than the transmitted beams and are substantially absorbed by the atmosphere before they have travelled any great distance.

Figure 4:
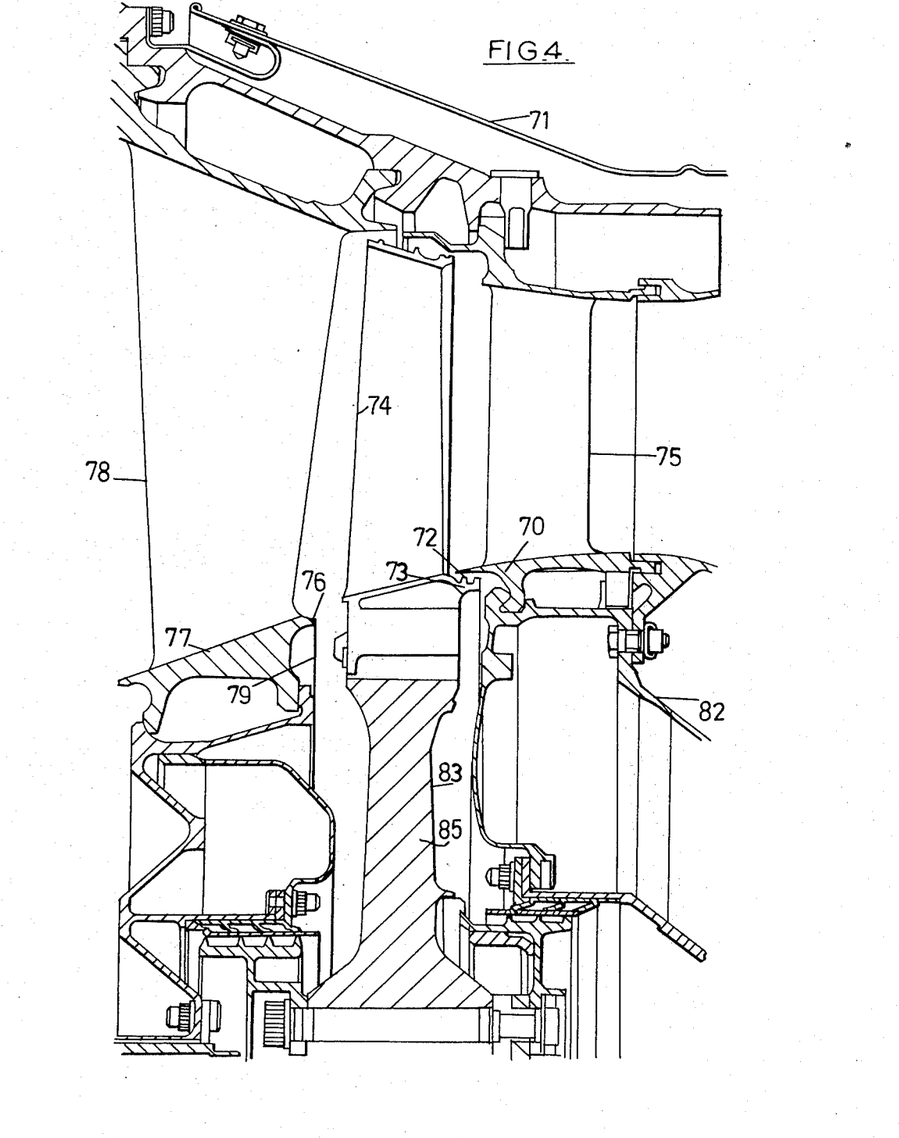
FIG. 4 is a drawing of a turbine section of a gas turbine engine.
Figure 5:
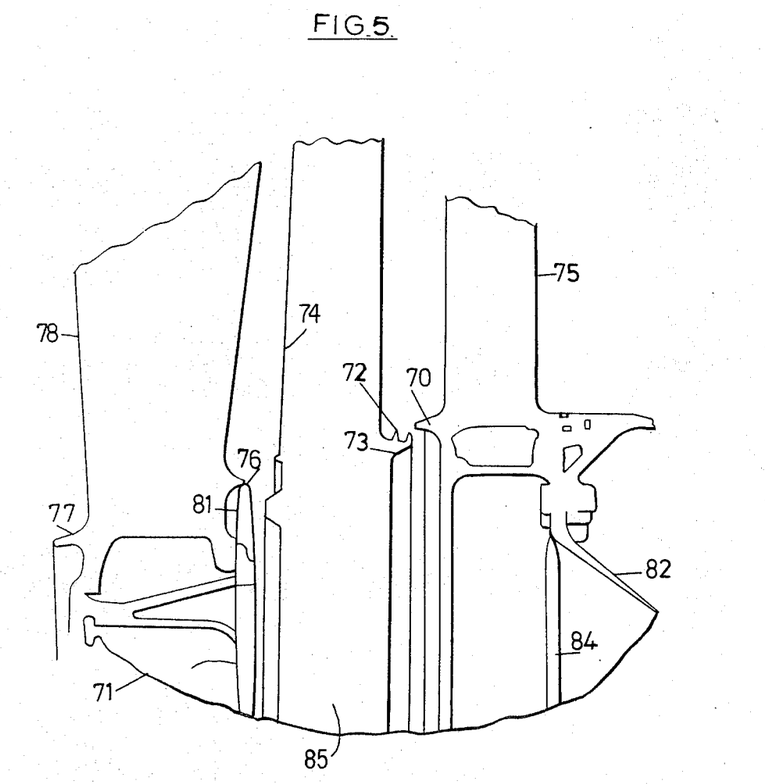
FIG. 5 is a radiographic view of the section of FIG. 4.

Reference is now made to FIGS. 4 and 5, which are a drawing and a radiographic view respectively of the turbine section 71 of a gas turbine engine. The normal ray 12 is directed towards the seal 72 between the platform 73 of the rotor blade 74 and the shroud 70 of the nozzle guide vane 75 in a direction tangential to the platform 73. The radiograph of FIG. 5 is one frame of the cine film taken midway through a small acceleration of the engine from idling to full power and represents one complete scanning of the fluorescent screen 13 of the light intensifier 14 which takes 0.04 sec, which corresponds to the standard scanning frequency of the Isocon television camera tube.

Because each frame is in fact a shadowradiograph the divergence of the X-ray beam as it traverses the engine produces a picture slightly different to the drawing of FIG. 5. These differences become more noticeable towards the outside edges of the picture. The edges 76 of the platforms 77 of the stator blades 78 downstream of the rotor blade 74 describe a complete circle and this circle seen edge on as a straight line 79 in FIG. 4 is seen as an ellipse 81 of very small minor diameter in FIG. 5. A comparision with similar ellipse 84 formed by the web 82 enables the point of incidence of the normal ray 12 to be interpolated so that its position may be adjusted to give the best possible picture of the feature (in this case the seal 72) which is being investigated.

It can clearly be seen by comparing the positions of the seal in FIGS. 4 and 5 that during the acceleration the seal has moved partially out of engagement with the shroud 70 on the nozzle guide vane. It might be thought a simple matter to calculate this positional change of a seal from the thermal gradients and coefficients of expansion of the engine casing and shafts. However, the thermal gradients are complex and indeterminate and of course movement of a seal such as is shown in the drawing will permit hot high pressure gas to leak along the front face 83 of the rotor disc 84, thus changing the thermal conditions and the gas loads from the design conditions. The technqiue of taking real time radiographs in a continuous recording has been found to yield greatly reduced development times for the engine by allowing the designer to assess deviations from his design conditions.

Figure 6:
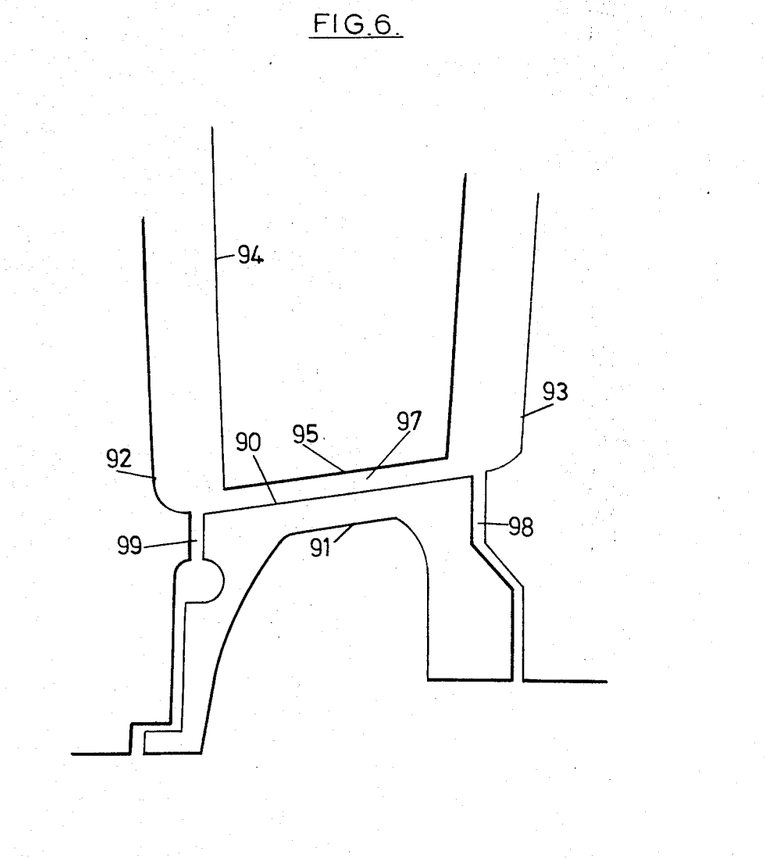
FIG. 6 illustrates a part of a compressor of a gas turbine engine for investigation by use of the invention.

Precise measurement of the gaps present in radiographs may be determined by the technique of micro densitometry illustrated by FIGS. 6, 7, 8 and 9. FIG. 6 shows a part section of a compressor rotor of a gas turbine engine, in particular a spacer 91 is situated between two compressor rotors 92, 93 respectively and forms the tip seal with a tip of stator blades 94. In operation evidence has been found of the tips 95 of the stator blades rubbing on the radially outer face 90 of the spacer. This was thought to be due to the two rotors coming together to take up the design clearances between the spacer ring and the rotors, thus compressing the spacer which then bowed in the middle and interfered with the tips of the stator blades.

Figure 7:
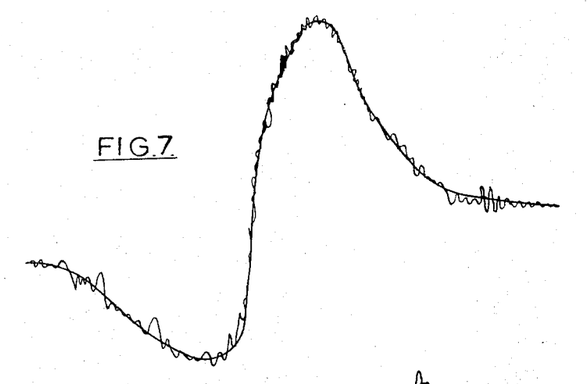
FIGS. 7, 8 and 9 are typical microdensitometer traces of the compressor of FIG. 6.
Figure 8:
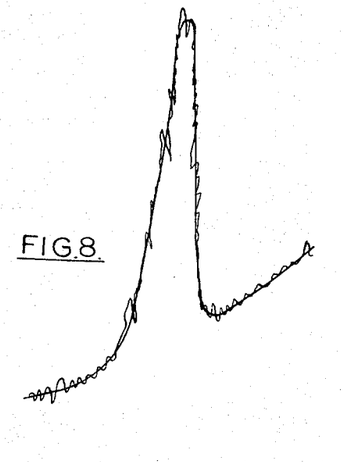
Figure 9:
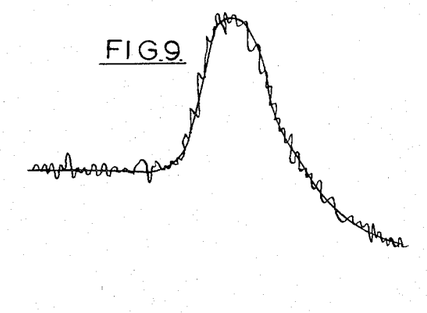
Figure 10:
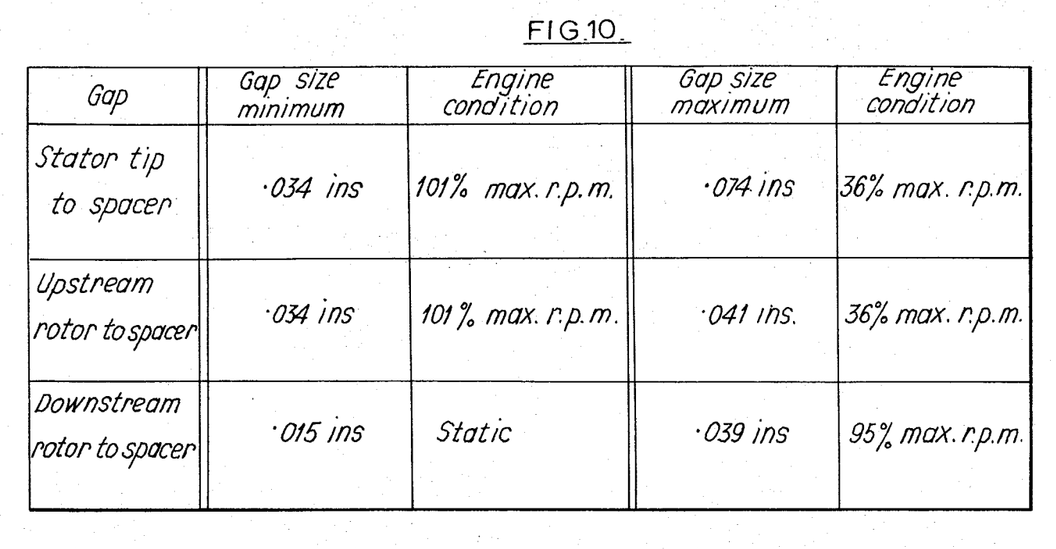
FIG. 10 is a table showing the variation in dimensions of the compressor of FIG. 6 measured from the microdensitometer traces of FIGS. 8, 9 and 10.

Three radiographic films were taken of the spacer ring during operation of the engine with the normal ray accurately aligned through each of the points 97, 98, 99 representing the clearances between the spacer and the stator tip and the front and rear faces of the two rotors respectively. Each radiograph was then examined and specific frames of the cine films measured with a microdensitometer to establish the variation in exposure across the gaps. The three typical microdensitometer traces are shown in FIGS. 7, 8 and 9 for the stator tip clearance and the front and rear gaps respectively. By comparision of several microdensitometer traces for each of the gaps at different operating conditions of the engine, the traces can be calibrated and accurate measurements of the gaps obtained. The table of FIG. 10 shows the maximum and minimum gap sizes found at varying operating conditions and illustrates the accuracy that may be achieved with this technique. For this particular installation measurement to one thousandth of an inch was possible. The interference of the stator tips and the spacer ring was subsequently identified as being due to a different cause than that suspected. To ensure the accurate line up of the normal ray, necessary for microdensitometry measurements, laser measuring techniques may be employed.

It will be understood that it is possible to pulse the electron gun of the linear accelerator in synchrony with the rotation of the engine, thus obtaining stroboscopic pictures and thereby freezing a particular blade or other rotating component for examination. Unfortunately, in a gas turbine engine the other blades and components in the same radial plane as the particular blade will reduce the definition of the picture but with, for example, a reciprocating piston engine, if the normal ray is directed radially through a cylinder bore the motion of the piston may be frozen and dimensions such as piston ring gap clearances measured.

To further improve the quality of recordings obtained from the engine, computer picture clean up techniques may be employed. One successful radiographic apparatus used has been a Radiation Dynamics, super X linear accelerator modified to remove the associated accessories from the proximity of the investigation thereby to avoid problems associated with noise and vibrations undesirably triggering relays etc., a Siemens Kruppa Screen of zinc cadmium sulphide and a De Oude Delft Delcalix SI 12.5 image intensifying system.

The techniques has been used by the applicants to examine a range of gas turbine engines from a 900 S.H.P. helicopter engine to a 40,000 lbf thrush high by pass gas turbine engine, a gain of one hundred S.H.P. was obtained with the helicopter engine within a few weeks of studying the operation of the seals on the radiographic film. Certain seals in other engines have been recorded in deflected and extended configurations considerably greater than the range of movements envisaged by the designers. The information gained from the use of the invention has enabled considerable reductions in development times to be made.

I claim:
1. Apparatus for obtaining a real-time sequence of images on a television receiver of the movement of the internal parts of an operating rotating turbine engine, comprising:
    means for directing radiation in the energy range of 5 – 12 MeV at a selected area of the engine, said radiation having a power greater than 250 rads per minute at a distance of one meter from the source of said radiation,
    a fluorescent screen for receiving the radiation transmitted through said engine and producing a fluorescent image,
    means for scanning said fluorescent screen at the scanning frequency of said television receiver,
    means coupling said scanning means to said television receiver for displaying said fluorescent image, and
    a video tape recorder coupled to said television receiver for recording said fluorescent image.

2. The apparatus defined by claim 1, which further includes intensifier means interposed between said fluorescent screen and said scanning means for intensifying said fluorescent image prior to the scanning thereof.

3. The apparatus defined by claim 2, which further comprises material surrounding said image intensifier isolating said intensifier from seismic and acoustic vibrations.

4. The apparatus defined by claim 1, which further comprises a filter adjacent said fluorescent screen between said image and said fluorescent screen.

5. The apparatus defined by claim 4, wherein said filter comprises a sheet of copper 0.05 centimeter thick.

6. A method of obtaining a real-time sequence of images on a television receiver of the movement of the internal parts of an operating rotating turbine engine, comprising the steps of:
    directing radiation in the energy range of 5 – 12 MeV at a selected area of engine, said radiation having a power greater than 250 rads per minute at a distance of one meter from the source of said radiation,
    receiving the radiation transmitted through said engine on a fluorescent screen to produce a fluorescent image,
    scanning said fluorescent image at the scanning frequency of said television receiver,
    displaying said fluorescent image on the screen of said television receiver, and
    recording the image received by said television receiver on a video tape recorder.

7. The method defined by claim 6, which further includes the step of intensifying said fluorescent image prior to the scanning thereof.

8. A method of investigating an engine as defined by claim 6, wherein said radiation is directed along a chord of said engine.

9. A method of investigating a turbine engine which comprises the steps of:
- directing radiation in the energy range of 5 – 12 MeV at a selected area of the engine, said radiation having a power greater than 250 rads per minute at a distance of one meter from the source of said radiation,
- receiving the radiation transmitted through said engine on a fluorescent screen to produce a fluorescent image,
- scanning said fluorescent image at the scanning frequency of said television receiver,
- displaying said fluorescent image on the screen of said television receiver,
- recording said fluorescent image on a photographic film, measuring the intensity distribution on said film and comparing this intensity distribution with either known static dimensional relationships of the parts of said engine corresponding to the image or with the intensity distributions of similar images measured at different operating conditions of said engine, and obtaining a numerical value for the dimensional relationship of the parts of said engine corresponding to the condition at which said amplified image was obtained.

10. A method of obtaining a real-time sequence of images on a television receiver of the movement of the internal parts of a rotatable turbine engine, comprising:
- setting up said engine on a test site,
- operating said engine under related running conditions,
- directing radiation in the energy range of 5 – 12 MeV at a selected area of the engine, said radiation having a power greater than 250 rads per minute at a distance of one meter from the source of said radiation,
- receiving the radiation transmitted through said engine on a fluorescent screen to produce a fluorescent image,
- intensifying said fluorescent image by means of an image intensifier,
- scanning said intensified image at the scanning frequency of said television receiver,
- providing radiation shielding around said image intensifier and around the test site for protecting operation of the engine and personnel in the vicinity of the test from harmful doses of radiation,
- displaying said image on the screen of said television receiver, and
- wrapping said image intensifier with material for isolating said intensifier from seismic and acoustic vibrations.

* * * * *